United States Patent [19]

Kamen et al.

[11] Patent Number: 5,200,172

[45] Date of Patent: Apr. 6, 1993

[54] COSMETIC PRODUCTS AND METHODS OF PRODUCING SAME

[75] Inventors: Melvin Kamen, Highlands, N.J.; Philip Bernstein, Yardley, Pa.

[73] Assignee: Revlon, Inc., New York, N.Y.

[21] Appl. No.: 628,612

[22] Filed: Dec. 17, 1990

Related U.S. Application Data

[63] Continuation-in-part of Ser. No. 296,230, Jan. 12, 1989, Pat. No. 4,978,524.

[51] Int. Cl.$^5$ .............................................. A61K 7/021
[52] U.S. Cl. ........................................ 424/64; 424/63; 424/78.03; 424/DIG. 5; 427/536; 427/490
[58] Field of Search ................ 424/64, 78, DIG. 5; 427/40, 41, 43.1

[56] References Cited

U.S. PATENT DOCUMENTS

| | | | |
|---|---|---|---|
| 3,403,040 | 9/1968 | Osipow et al. | 424/64 |
| 4,072,769 | 2/1978 | Lidel | 427/38 |
| 4,188,426 | 2/1980 | Auerbach | 424/40 |
| 4,264,750 | 4/1981 | Anand | 525/356 |
| 4,296,151 | 10/1981 | Boultinghouse | 427/255.1 |
| 4,404,256 | 9/1983 | Anand | 428/409 |
| 4,467,075 | 8/1984 | Tarancon | 525/356 |
| 4,491,653 | 1/1985 | McGinniss | 525/356 |
| 4,508,701 | 4/1985 | Yagi | 427/40 |
| 4,557,945 | 12/1985 | Yagi et al. | 427/40 |
| 4,593,050 | 6/1986 | Cohen . | |
| 4,801,445 | 1/1989 | Fukui et al. | 424/69 |
| 4,844,986 | 7/1989 | Karakelle et al. | 427/41 |

FOREIGN PATENT DOCUMENTS 5099932  7/1980  Japan .
765545  1/1957  United Kingdom .

*Primary Examiner*—Thurman K. Page
*Assistant Examiner*—A. Hulina
*Attorney, Agent, or Firm*—Julie Blackburn

[57] ABSTRACT

A hydrocarbonous-based cosmetic product, such as a lipstick, has its surface treated by means of a plasma treatment process employing a halogen gas. The treated (i.e., halogenated) surface has a uniform, satin-matte finish, as well as a lower wetting angle with respect to certain materials capable of providing the cosmetic product with an ultra-glossy finish. Thus, if such materials are subsequently applied to the halogenated surface of the cosmetic product, the cosmetic product can be provided with an ultra-glossy finish.

6 Claims, 3 Drawing Sheets

COSMETIC PRODUCTS AND METHODS OF PRODUCING SAME

CROSS-REFERENCE TO RELATED APPLICATION

This application is a continuation-in-part of copending application Ser. No. 07/296,230, filed Jan. 12, 1989 now U.S. Pat. No. 4,978,524.

FIELD OF THE INVENTION

The present invention relates to hydrocarbonous-based cosmetic products having either an ultra-glossy (i.e., "wet look") finish, or a uniform, satin-matte finish and, to the respective methods for providing such products.

BACKGROUND OF THE INVENTION

In the manufacture of lipstick and other hydrocarbonous-based cosmetic products, a molding process is conventionally used. As a result of the adhesion between the cosmetic product and the mold, problems are often encountered in releasing the cosmetic product from the mold. The poor release of the cosmetic product from the mold often causes the cosmetic product to have a non-uniform matte finish (i.e., a finish which is flat or dull and characterized by numerous surface irregularities). Because such a non-uniform matte finish gives cosmetic products a non-cosmetic appearance, efforts have been made to provide cosmetic products with a more uniform (i.e., a more cosmetic) appearance.

One common technique for eliminating the non-uniform matte finish on molded lipstick involves "flaming" the lipstick after it has been removed from the mold. While flaming has been found to improve the finish of the lipstick, the degree of improvement is limited. Flaming is also disadvantageous because it results in a relatively high percentage of "rejects". Moreover, some lipsticks, such as those with molded indicia or those with low melting temperatures, are not suitable for flaming. Thus, there is a real need for an alternate post-molding treatment technique for lipstick which improves the matte finish of the molded product without inhibiting further processing in the event that a different finish, such as a glossy or "wet look" finish, is desired.

SUMMARY OF THE INVENTION

In accordance with one aspect of the present invention, a hydrocarbonous-based cosmetic product is provided with an ionically-halogenated surface having a uniform, satin-matte finish. More particularly, the halogenated surface may comprise fluorinated hydrocarbons formed by subjecting the cosmetic product to a plasma treatment process involving the use of a fluoro-compound and a reactor gas in the presence of an electromagnetic field, such as a cold-glow discharge. It has been found that such a halogenated surface provides the cosmetic product with a uniform, satin-matte finish, which eliminates the necessity of flaming the cosmetic product to improve its finish.

In accordance with another aspect of the present invention, the halogenated surface of the cosmetic product has a wetting angle which is less than its normal wetting angle (at least with respect to certain coatings). Thus, a material having an ultra-glossy finish and having poor adhesion with objects which have a wetting angle in the neighborhood of the normal wetting angle of the cosmetic product can be applied to the cosmetic product to give it an ultra-glossy (i.e., "wet look") finish.

BRIEF DESCRIPTION OF THE DRAWINGS

For a better understanding of the present invention, reference is made to the following detailed description of various exemplary embodiments considered in conjunction with the accompanying drawings, in which.

DETAILED DESCRIPTION OF THE EXEMPLARY EMBODIMENTS

Although the present invention has applicability to many different hydrocarbonous-based cosmetic products, such as the marking cores of eyeliner pencils and cream eyemarker pens, it is especially suitable for use in connection with lipstick products. Accordingly, the present invention will be described below in connection with lipstick products.

Figure 1:
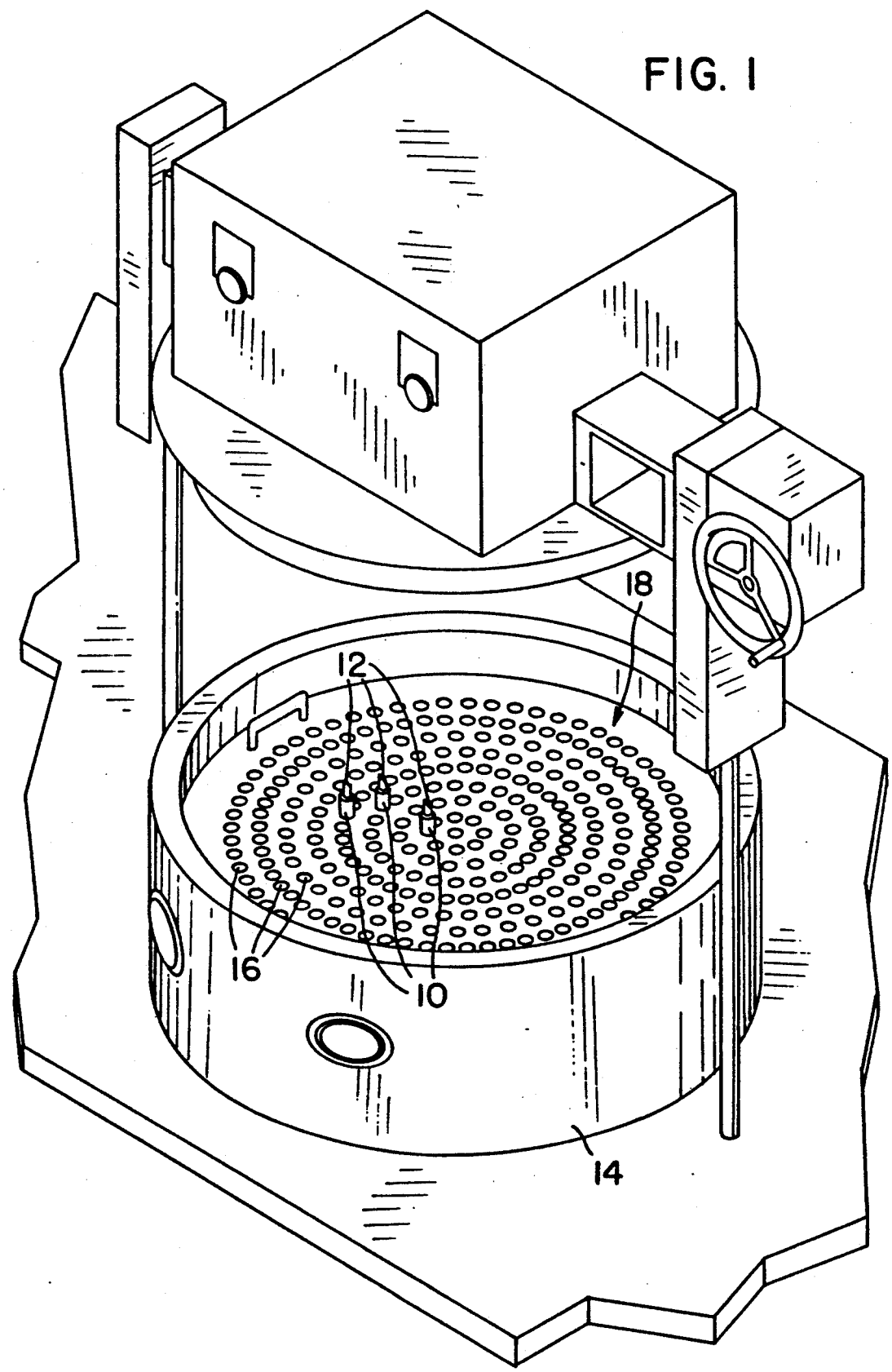
FIG. 1 is a detailed perspective view of a vacuum chamber which is used in connection with a chemical vapor deposition system illustrated diagrammatically in FIG. 3, the vacuum chamber being shown in its open position in order to facilitate consideration and discussion.
Figure 2:
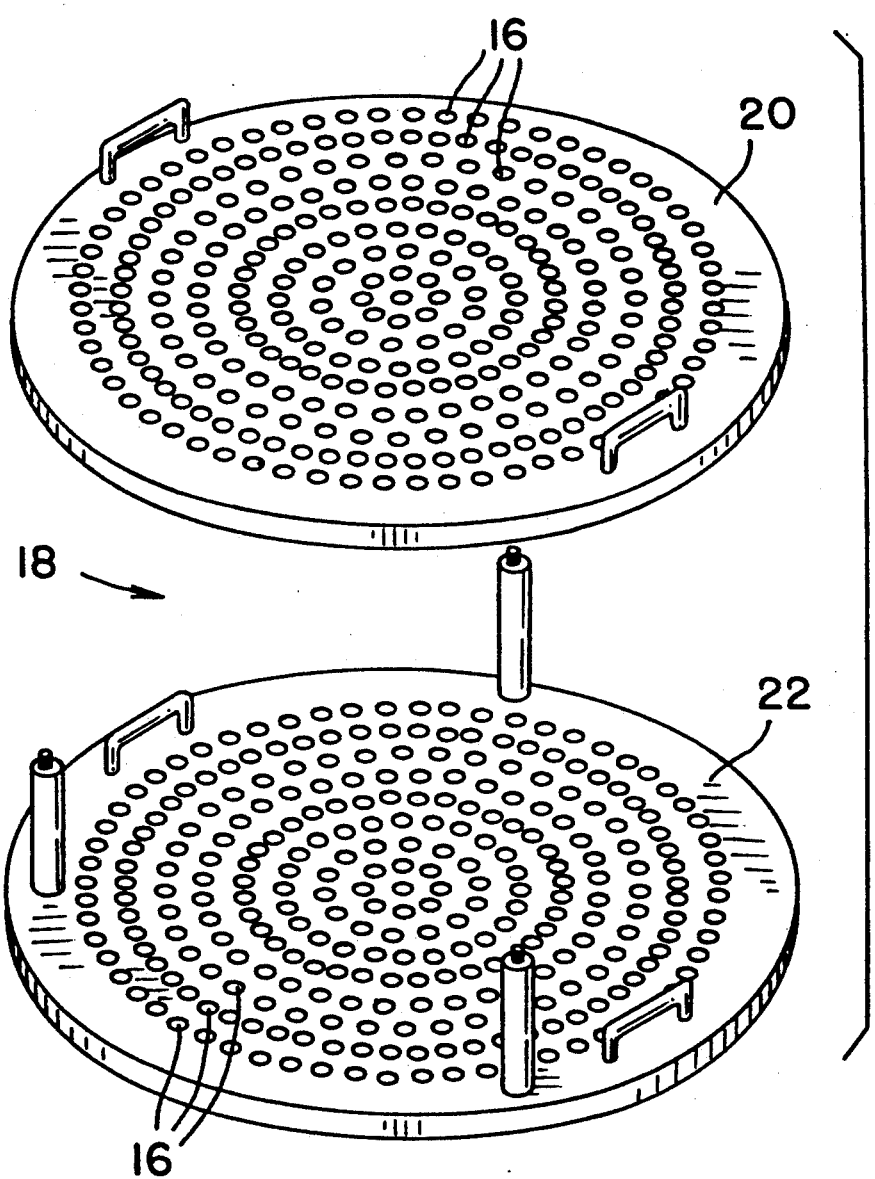
FIG. 2 is an exploded perspective view of a fixture which is used in the vacuum chamber illustrated in FIG. 1.

With reference to FIG. 1, sticks 10 of lipstick 12 are mounted in an upright position in a vacuum chamber 14. The sticks 10 are received in openings 16 provided in a fixture 18, which is removably mounted in the vacuum chamber 14. When the vacuum chamber 14 is operating at full capacity, all of the openings 16 in the fixture 18 would receive a stick 10 of lipstick 12. In order to maximize the capacity of the vacuum chamber 14, the fixture 18 has a tiered construction (see FIG. 2), whereby the fixture 18 includes an upper tier 20 and a lower tier 22. Once the vacuum chamber 14 has been loaded, it is closed in preparation for the performance of a plasma treatment process using a chemical vapor deposition system 24 (see FIG. 3).

Figure 3:
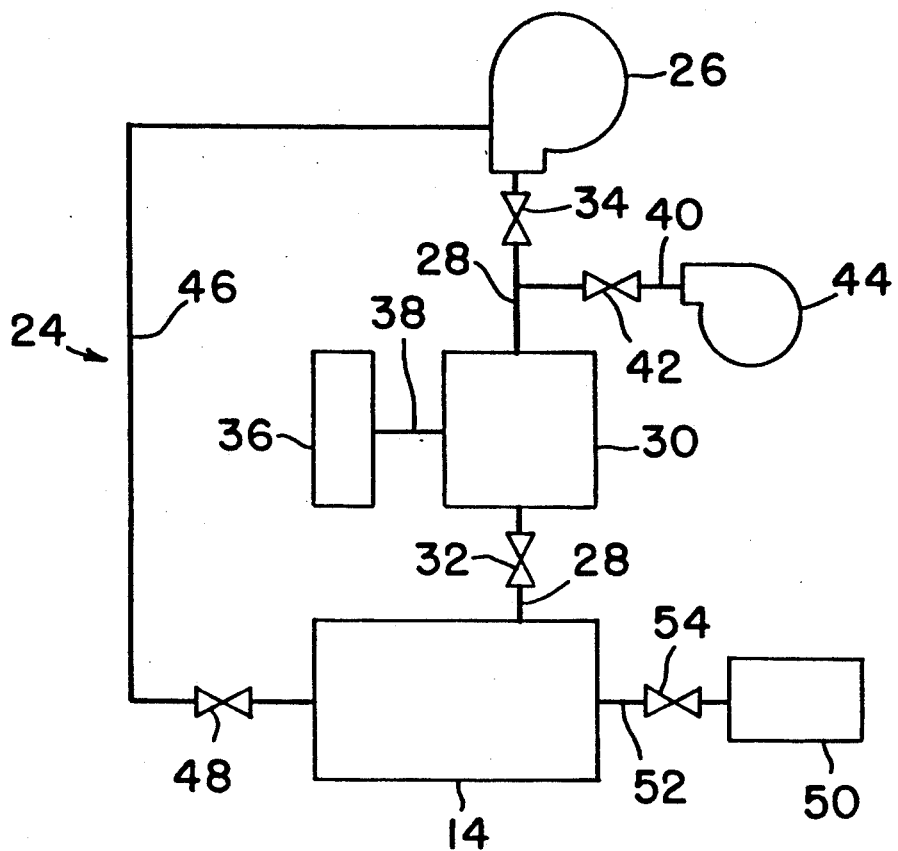
FIG. 3 is a flow diagram of a system which incorporates the vacuum chamber illustrated in FIG. 1 and which performs a plasma treatment process for providing lipsticks with uniform, satin-matte finishes in accordance with one aspect of the present invention.

Referring now to FIG. 3, the chemical vapor deposition system 24 includes, in addition to the vacuum chamber 14, a vacuum pump 26, which is connected to the vacuum chamber 14 by a foreline 28. A cold trap 30 is positioned in the foreline 28 between the vacuum chamber 14 and the vacuum pump 26. The foreline 28 includes a valve 32 between the vacuum chamber 14 and the cold trap 30. Another valve 34 is positioned in the foreline 28 between the vacuum pump 26 and the cold trap 30. A refrigerant unit 36 supplies refrigerant to the cold trap 30 through a line 38. A line 40, which is provided with a valve 42, connects a holding pump 44 to the foreline 28 between the valve 34 and the cold trap 30. The vacuum pump 26 is also connected to the vacuum chamber 14 by a roughing line 46, which includes a valve 48. Treatment gas is supplied from a source 50 to the vacuum chamber 14 through a line 52, which includes a valve 54.

With the valves 42 and 48 open and the valves 32, 34 and 54 closed, the vacuum chamber 14 is evacuated through the roughing line 46 by the vacuum pump 26 until a vacuum measurement of 50 microns or less is achieved. After such a vacuum has been created in the vacuum chamber 14, the valves 42 and 48 are closed and the valves 32 and 34 are opened. When a vacuum measurement of 5 microns or less is reached, the valve 54 is opened to permit treatment gas, such as $C_2F_4$, $SiF_4$, $F_2$, $CF_4$ or the like, to bleed into the vacuum chamber 14 until a vacuum measurement of about 50 microns is reached.

The treatment gas is maintained in the vacuum chamber 14 for a length of time, usually about 2 to 15 minutes, sufficient to permit the treatment gas to saturate the surface of the lipstick 12 contained in the vacuum chamber 14. At the end of the saturation period, the cathode (not shown) of the vacuum chamber 14 is energized to generate a plasma throughout the vacuum chamber 14. The plasma, in turn, causes a chemical reaction between the treatment gas and the lipstick 12. As a result of such a chemical reaction, the surface composition of the lipstick 12 is modified so as to obtain a surface layer 54 (see FIG. 4) having a wetting angle which is different from the normal wetting angle of the lipstick, as well as cladding-like characteristics which will be discussed hereinafter. Typically, the surface layer 54 has a thickness in a range of from about 10 angstroms to about 300 angstroms.

The vehicular gas useful in the plasma treatment process described above could be any inert, oxygen-free gas. For the purposes of this invention, it is preferred that helium be utilized in combination with fluorine. In fact, any plasma reactive gas capable of bonding (chemically and possibly mechanically) to the surface of the lipstick 12 could be used as the treatment gas. Even non-plasma reactive gasses might be employed as the treatment gas.

If the treatment gas is $C_2F_4$ (tetrafluoroethylene), $C_2F_6$ (perfluoroethane), $SiF_4$ (silicontetrafluoride), $F_2$ (fluorine), $CF_4$ (tetrafluoromethane) or the like, the surface layer 54 would be more wettable to non-polar compounds, such as fluorinated oils, etc. By using air as the treatment gas, the surface layer 54 would be more wettable to polar compounds, such as water, alcohol, etc.

At the conclusion of the plasma treatment process (usually about 2 to 15 minutes), the valves 32 and 34 are closed, while the valve 54 is left open until the pressure within the vacuum chamber 14 is adjusted to that of air, i.e., atmospheric pressure. Now, the valve 54 can be closed and the vacuum chamber 14 can be opened. After opening the vacuum chamber 14, the sticks 10, with their plasma-treated lipsticks 12, are removed from the fixtures 18. Because the plasma treatment is conducted at room temperature, the lipsticks 12 do not undergo any appreciable distortion.

Due to the fact that some lipsticks contain moisture, the cold trap 30, which is maintained under vacuum at all times by either the vacuum pump 26 or the holding pump 44, must be employed to collect any moisture removed from the lipsticks 12 during the evacuation of the vacuum chamber 14 and thereby prevent such moisture from contaminating the vacuum pump 26. Actually, moisture is removed from the boundary of the lipsticks 12 only, leaving the interior of the lipsticks 12 with basically the same moisture content that they had prior to the performance of the plasma treatment process described above.

Figure 4:
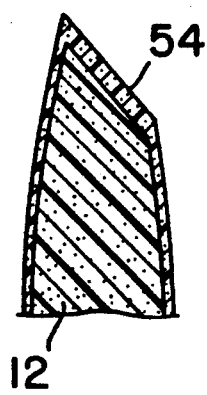
FIG. 4 is a is a cross-sectional view of lipstick which has undergone treatment by the system illustrated in FIG. 3.

FIG. 4 is a cross-sectional view of the plasma treated lipstick 12, having the ionically halogenated surface layer 56 formed thereon. The surface layer 56 provides the lipstick 12 with a uniform, satin-matte finish and, accordingly, is useful as a final product when such a finish is desired. If an ultra-glossy product is desired, the plasma-treated lipstick 12 would have to undergo further processing as described below.

Figure 5:
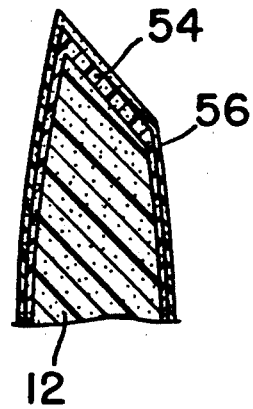
FIG. 5 is a cross-sectional view of the lipstick illustrated in FIG. 4 after undergoing a further treatment step in accordance with another aspect of the present invention.

With reference to FIG. 5, a fluorosilicone outer layer 58 has been applied to the surface layer 56 of the lipstick 12 shown in FIG. 4. Because fluorosilicone and most, if not all, of the other suitable silicone derivatives are hydrophobic and soluble in castor oil, and most lipstick formulations include castor oil, the surface layer 56 is necessary to function as a cladding-like barrier between the rest of the lipstick 12 and the outer layer 58, thereby protecting the rest of the lipstick 12 from the fluorosilicone contained in the outer layer 58. Also, the waxes, castor oil and wetting agents commonly found in lipstick formulations tend to repel silicone and most, if not all, of the other suitable silicone derivatives. By plasma treating the lipstick 12, its wetting angle is decreased (at least with respect to the fluorosilicone) as result of the formation of the surface layer 56, thereby providing the required adhesion between the lipstick 12 and the outer layer 58.

One method of forming the outer layer 58 involves dipping the plasma-treated lipstick 12 into a mixture which is about 10% to 20% solids, by weight, silicone oil or fluorinated silicone and about 80% to 90%, by weight, Freon or other suitable solvent which promotes the drying of the silicone, or fluorinated silicone. Such a method also provides a means for controlling the thickness of the outer layer 58. The resulting outer 58, which covers the entire exterior surface of the plasma-treated lipstick 12, has a thickness in a range of from about 0.1 microns to about 0.2 microns. An alternate method of forming the outer layer 58 involves applying a drop of silicone directly to the tip of the plasma-treated lipstick 12 and then allowing the silicone to migrate over the entire exterior surface thereof. It would also be possible to spray the silicone directly onto the plasma-treated lipstick 12.

Among the silicone compounds useful in the post-halogenation step described above are those polyfluorosilicones represented by the following general structural formula:

(A) (B) (C) SiO—(Si(D)(E)O)$_x$—Si (A) (B) (C) wherein A, B and C are the same or different and each represents a $C_{1-4}$ alkyl group one of which is optionally substituted with 1, 2 or 3 fluorine atoms, or a $(CH_3)_3SiO$-group; and wherein D and E are the same or different and represent $C_{1-4}$ alkyl, phenyl, $(CH_3)_3SiO—$, or alkyl substituted with $C_{1-4}$ alkoxy or with 1, 2 or 3 fluorine atoms; and Wherein x is a value such that the compound is liquid or solid at room temperature. Additional preferred silicone compounds include those in which A, B, C, D and E are methyl ("dimethicone"), and fluorosilicone FS-1265. More broadly, satisfactory silicones are those which are inert to the treated cosmetic product surface, wet the treated surface, and provide the highly reflective glossy surface finish when applied as taught herein. Such a finish might also be obtained using hydrocarbon oils, such as mineral oil, vegetable oils, such as castor oil, lanolin, fatty alcohols and esters, and saturated alcohols and esters.

In a further alternate embodiment of this invention, a molded cosmetic product having volatile ingredients therein can be subjected to controlled flaming prior to the halogenation process. In such instances, the flaming step is limited to prevent out-gassing, i.e., the migration of the volatile ingredients to the surface of the cosmetic product. Subsequent treatment of the flamed surface by means of the halogenation process described above yields a barrier-like, protective coating thereon. The resultant protective coating appears in the form of the satin-matte finish discussed hereinabove.

In a yet further embodiment of this invention a molded cosmetic product can be prepared wherein a portion of the surface thereof has an ultra-glossy finish, while the remaining portion thereof has a satin-matte finish. The preparation of such a cosmetic product having a "combination finish" would involve masking those halogenated areas which are to remain satin-matte finished prior to treating the exposed areas with the fluorosilicone solution, or any other suitable solution, to obtain an ultra-glossy finish.

The following examples further illustrate certain aspects of the present invention and are not intended to limit the scope thereof to such.

EXAMPLE I

Three hydrocarbonous-based, molded lipstick products were prepared in accordance with this invention. Three molded lipstick bullets were prepared, using conventional formulations and molding techniques. In each instance, the lipstick formulation essentially comprised, based on the weight of the total composition, 60–75 percent oil, 20–25 percent wax, 5–10 percent fatty material, 5–10 percent polyhydroxy alcohol, and, at least, from 5 to 10 percent color additive(s). The molded lipstick products were each placed in a respective opening 16 within the fixture 18 shown in FIG. 2, which in turn was positioned within the vacuum chamber 14 illustrated in FIG. 1. The vacuum chamber 14, having the fixture 18 positioned therein, was incorporated within a chemical vapor system similar to that illustrated in FIG. 3, wherein the surface fluorination process according to this invention was carried out as follows:

The lipstick products positioned as described hereinabove were treated with a gas essentially comprised of about 5 percent, by volume, of methylfluoride (Tetrafluoromethane) in helium which was introduced into the vacuum chamber. Initially, the vacuum pressure was gradually adjusted to a level of 50 microns or less and thereafter adjusted to a level of between 5 microns or less. The contents of the vacuum chamber were then flushed with helium gas which was introduced up to a level of between 200 to about 1,000 microns. After a period of about five minutes, the vacuum chamber was re-evacuated to a pressure of between 5 to about 50 microns. The fluorinated gas was then introduced into the vacuum chamber and maintained therein for a period of between 30 seconds and 15 minutes so as to allow complete saturation of the fluorine ions throughout the surface of the lipstick products. Upon completion of the fluoromethane saturation, a cold glow discharge was generated, at a power of between 15 to about 18 Watts, throughout the vacuum chamber by means of direct electrical excitation of the treatment gas, thus initiating the chemical reaction of the plasma with the surfaces of the lipstick products. The plasma treatment was carried out over a period of from 5 to about 60 minutes. Thereafter, the pressure within the vacuum chamber was readjusted to ambient conditions. The treated lipstick products were then removed from the fixture. The resultant products displayed uniform satin-matte surfaces.

Subsequent testing, using a conventional ESCA apparatus, indicated that the surfaces of the lipstick products had been fluorinated to a thickness of from between 500 and 2,000 Angstroms. In addition, the wetting angles had been increased from between 70–80 to about 120–130 degrees, using a goniometer and formalin (an acqueous solution containing 37 percent, by weight, of formaldehydge and from 10 to 15 percent, by volume, of methanol) as the test solution. The wetting angle (or contact angle) is the measurement of the angle which exists between a liquid and a solid surface. This measurement gives an indication of the relative values of the forces of adhesion and cohesion that result in interfacial tension. As used herein, the term "wetting angle" describes the ability of a specified solid surface (i.e., the cosmetic product) to be wet by a specified liquid under defined conditions. Thus, the smaller the wetting angle of the cosmetic product, the greater is the "wettability" of its surface by the specified liquid and vice versa. (A more detailed discussion of the concept of the contact angle as a useful inverse measure of spreadability or wettability is presented by Zisman, Advances in Chemistry Series, Ch. 1, Equilibrium Contact Angle.)

The surfaces of the molded lipstick products described hereinabove were subsequently coated with a commercially available fluorosilicone oil and alcohol solution to produce ultra-glossy finishes. More particularly, FS-1265 (a fluorosilicone oil and alcohol solution produced by the Dow Corning Company) was utilized as the post-halogenation treatment material. In each instance, a single drop of the aforesaid fluorosilicone oil and alcohol solution was applied to the halogenated surface of the lipstick products and closely monitored for over a period of several days. Initially, the alcohol fluorosilicone oil solution quickly spread flat and formed an ultra-glossy coating over the halogenated surfaces of each of the lipstick products. After four days, it was observed that no penetration of the surfaces of the lipstick products by the fluorosilicone oil solution had occurred. Accordingly, the ultra-glossy finishes of the final lipstick products remained unchanged after several days.

Prior tests conducted on unhalogenated lipstick products showed that the alcohol fluorosilicone oil solution would tend to form beads on the surfaces of such lipstick products, thereby indicating that the lipstick products were not wetted by the alcohol fluorosilicone oil solution (i.e., they exhibited poor wettability). In view of the fact that the wettability tests conducted with formalin exhibited increased wetting angles and therefore decreased wettability, the increased wettability of the halogenated lipstick products by the alcohol fluorosilicone oil solution was a surprising and unexpected result.

EXAMPLES II–VIII

The procedural steps outlined in Example I hereinabove were repeated, except that the surfaces of seven lipstick products having slightly varied formulations were treated with a similar halogenated gas plasma prior to being coated with a fluorosilicone solution similar to that utilized in Example I, supra. In the preparations of the present series, the power levels, i.e., wattages, and the reaction pressures, within the vacuum chamber were varied. Also, in one instance, the reaction time was significantly decreased. Tetrafluoroethylene was utilized as the halogenating compound throughout the series, along with helium as the carrier gas during the plasma treatment. Helium was also used to flush the vacuum chamber before and after each halogenation procedure. The varied conditions and resultant wetting angle values as determined in the manner discussed hereinabove are set forth in the following chart:

TABLE I

| Example No. | Halogenation Reaction Conditions | | | Wetting Angle(s) (degrees) | |
|---|---|---|---|---|---|
| | Power (watts) | Pressure ($\mu$)* | Time (min.) | Pre-Reaction | Post-Reaction |
| II | 18 | 20 | 30 | 95 | 132–146 |
| III | 18 | 14 | 30 | 95 | 132–142 |
| IV | 18 | 5 | 30 | 95 | 118–128 |
| V | 50 | 50 | 2 | 73 | 103 |
| VI | 15 | 14 | 30 | 75 | 150–160 |
| VII | 18 | 15 | 30 | 70–80 | 140 |
| VIII | 18 | 19 | 30 | 95 | 130–135 |

*(Microns)

As indicated in Table 1 above, the wetting angles in Examples II–VIII increased when formalin was used as the test solution. However, consistent with the results reported above with respect to Example I, the wetting angles surprisingly and unexpectedly decreased when the halogenated lipstick products were treated with an alcohol fluorosilicone oil solution in the manner set forth in Example I above. The resultant lipstick products similarly exhibited uniform, ultra-glossy finishes which were superior to conventional lipstick products. Moreover, based on conventional ESCA measurements (as discussed hereinabove), it was determined that the respective surfaces of the lipstick sticks had been halogenated to a thickness ranging from 1,000 to 2,000 Angstroms.

EXAMPLE IX

A molded cosmetic product having a uniform, satin-matte finish was prepared, in accordance with this invention. More specifically, a lipstick product having such a finish was prepared as follows:

A molded lipstick product was prepared, using conventional formulation and molding techniques. In this instance, the lipstick formulation essentially comprised, based on the total weight of the composition, about 60 percent of oil, 20 percent of wax, 8 percent of a fatty material, 7 percent of a polyhydroxy alcohol, and about 5 percent of a commercially available color additive. The resultant lipstick product was placed in an opening 16 within the fixture 18 shown in FIG. 2, which in turn was positioned within the vacuum chamber 14 illustrated in FIG. 1. The vacuum chamber 14, having the fixture 18 positioned therein, was incorporated within a chemical vapor system similar to that illustrated in FIG. 3. The fluorination process was thereafter carried out as follows The lipstick product positioned as described herein was treated with a gas essentially comprised of about 20 percent, by weight, of methylfluoride (tetrafluoromethane) in helium which was introduced into the vacuum chamber. Initially, the vacuum pressure was gradually adjusted to a level of 50 microns or less and thereafter adjusted to a level of between 5 microns or less. The contents of the vacuum chamber were then flushed with helium gas which was introduced up to a level of between 200 to about 1,000 microns. After a period of about five minutes, the vacuum chamber was re-evacuated to a pressure of between 5 to about 50 microns. The fluorinated gas was then introduced into the vacuum chamber and maintained therein for a period of between 30 seconds and 15 minutes so as to allow complete saturation of the fluorine ions throughout the surface of the lipstick product. Upon completion of the fluoromethane saturation, a cold glow discharge was generated, at a power of 25 Watts, chamber by means of direct electrical excitation of the treatment gas, thus initiating the chemical reaction of the plasma with the surface of the lipstick product. The plasma treatment was carried out over a period of about 5 minutes. Thereafter, the pressure within the vacuum chamber was readjusted to ambient conditions and the treated lipstick product was removed from the fixture. The surface of the resultant product displayed a uniform satin-matte finish.

Both the ultra-glossy finished cosmetic products and those having satin-matte finishes offer aesthetic advantages, especially for point of sale purposes. After at least its initial application, it is possible that the silicone-coated lipstick, i.e., ultra-glossy finished products, could provide the user with a "wet look" and/or could inhibit chapping of the user's lips. It is also possible that the silicone from the outer layer could migrate into the inner layer after its initial use, whereby the foregoing advantages might be realized during subsequent uses of the lipstick.

Based on the disclosure set forth hereinabove, it will be understood that the embodiments described herein are merely exemplary. It will become apparent to those skilled in the art that various modifications in procedures, proportions, and materiels may be made, without departing from the spirit and scope of the invention. All such modifications and variations are intended to be included within the scope of the invention as defined by the following claims.

We claim:

1. A method of providing a cosmetic product comprising 60–75% oil, 20–25% wax, 5–10% fatty material, 5–10% polyhydroxy alcohol, and 5–10% color additives, with a 100–300 angstrom thick uniform, satin-matte finish of fluorinated hydrocarbons comprising the step of ionically fluorinating the surface of said cosmetic product using a plasma treatment process wherein the gas plasma reacts with the surface of the cosmetic product to provide a uniform satin-matte finish.

2. A method according to claim 1, wherein said plasma treatment process is carried out using a gas selected from a group consisting of $C_2F_4$, $C_2F_6$, $SiF_4$, $F_2$, and $CF_4$.

3. A method according to claim 1, wherein said molded cosmetic product is a lipstick.

4. A method according to claim 1, wherein said molded cosmetic product is the marking core of an eyeliner pencil.

5. A method according to claim 1 wherein said molded cosmetic product is the marking core of a creme eyemarker pen.

6. A method of providing a cosmetic product comprising 60–75% oil, 20–25% wax, 5–10% fatty material, 5-10% polyhydroxy alcohol, and 5-10% color additives, with a 100-300 angstrom thick ultra-glossy finish, which finish is applied by subjecting said cosmetic product to a plasma treatment process wherein the gas plasma reacts with the lipstick surface to provide said finish, comprising the steps of:

fluorinating the surface of said cosmetic product which has a first wetting angle to thereby produce a first layer having a second wetting angle which is less than said first wetting angle, said fluorinating step being carried out using fluorine or a compound selected from a group consisting of silicon-tetrafluoride, perfluoroethane, tetrafluoroethylene, and tetrafluoromethane; and coating said first layer with a material having an ultra-glossy finish and having poor adhesion with objects having a wetting angle in the neighborhood of said first wetting angle, said material being selected from a group consisting of those polyfluoro-organo compounds represented by the following general formula:

$$(A)(B)(C) \text{SiO}-(\text{Si}(D)(E)\text{O})_x-\text{Si}(A)(B)(C)$$

wherein A, B, and C are the same or different and each represents a $C_{1-4}$ alkyl group one of which is optionally substituted with 1, 2, or 3 fluorine atoms, or a $(CH_3)_3Si-O-$group; and wherein D and E are the same or different and represent $C_{1-4}$ alkyl, phenyl, $(CH_3)_3SiO-$, or alkyl substituted with $C_{1-4}$ alkoxy, or with 1, 2, or 3 fluorine atoms; and wherein x is a value such that the compound is liquid or solid at room temperature.

* * * * *